(12) United States Patent
Gjerde et al.

(10) Patent No.: US 6,642,374 B2
(45) Date of Patent: Nov. 4, 2003

(54) PROCESS FOR SEPARATION OF POLYNUCLEOTIDE FRAGMENTS

(75) Inventors: Douglas T. Gjerde, Saratoga, CA (US); Robert M. Haefele, Campbell, CA (US); Paul D. Taylor, Gilroy, CA (US)

(73) Assignee: Transgenomic, Inc., Omaha, NE (US)

( * ) Notice: Subject to any disclaimer, the term of this patent is extended or adjusted under 35 U.S.C. 154(b) by 5 days.

(21) Appl. No.: 09/764,041

(22) Filed: Jan. 16, 2001

(65) Prior Publication Data

US 2001/0023290 A1 Sep. 20, 2001

Related U.S. Application Data

(63) Continuation of application No. 09/391,963, filed on Sep. 8, 1999, now Pat. No. 6,177,559, which is a continuation of application No. 09/065,913, filed on Apr. 24, 1998, now Pat. No. 5,986,085.
(60) Provisional application No. 60/044,856, filed on Apr. 25, 1997.

(51) Int. Cl.[7] .......... C07H 21/00; C07H 21/02; C07H 21/04

(52) U.S. Cl. .......... 536/25.41; 536/25.4

(58) Field of Search .......... 536/25.4, 25.41

(56) References Cited

U.S. PATENT DOCUMENTS

| | | | |
|---|---|---|---|
| 4,906,378 A | 3/1990 | Hagen et al. | 210/635 |
| 4,997,927 A | 3/1991 | Blocker et al. | 536/27 |
| 5,075,430 A | 12/1991 | Little | |
| 5,098,539 A | 3/1992 | Shieh | 204/182.8 |
| 5,203,992 A | 4/1993 | Drouen | 210/198.2 |
| 5,338,448 A | 8/1994 | Gjerde | 210/198.2 |
| 5,340,452 A | 8/1994 | Brenner | 204/180.1 |
| 5,413,708 A | 5/1995 | Huse | |
| 5,413,762 A | 5/1995 | Hirano et al. | 422/70 |
| 5,437,979 A | 8/1995 | Rampal | 435/6 |
| 5,443,734 A | 8/1995 | Fetner | 210/656 |
| 5,508,204 A | 4/1996 | Norman | 436/161 |
| 5,585,236 A | 12/1996 | Bonn et al. | 435/5 |

(List continued on next page.)

FOREIGN PATENT DOCUMENTS

| | | |
|---|---|---|
| EP | 0 507 591 A2 | 10/1992 |
| JP | 6-169754 | 6/1994 |
| JP | 7-170981 | 7/1995 |
| SU | 1759842 A1 | 9/1992 |

(List continued on next page.)

OTHER PUBLICATIONS

Gelfi et al, Detection of Point Mutations by Capillary Electrophoresis in Liquid Polymers in Temporal Thermal Gradients, Electrophoresis, vol. 15, No. 12, (Dec. 1, 1994) pp. 1506–1511.

Huber et al. Rapid and Accurate Sizing of DNA Framents by Ion–Pair Chromatography on Alkylated Nonporous Poly-(Styrene–Divinylbenzene) Particles, Analytical Chemistry, US, American Chemical Society, Columbus, vol. 67, (Feb. 1, 1995), pp. 578–585

Kuklin et al, A Novel Technique for Rapid Automated Genotyping of DNA Polymorphisms in the Mouse, Molecular and Cellular Probes, vol. 13, No. 3, (Jun. 1999) pp. 239–242.

Myers et al, Modification of the Melting Properties of Duplex DNA by Attachment of a GC–Rich DNA Sequence as Determined by Denaturing Gradient Gel Electrophoresis, Nucleic Acids Research, GB, Oxford, University Press, Surrey, vol. 13, No. 9 (1985) pp. 3111–3129.

Arnold, et al., A Highly Sensitive, Fast, and Economical Technique for Mutation Analysis in Hereditary Breast and Ovarian Cancers, Human Mutation, 14:333–339, (1999).

Belenky et al. High–Throughput Biopolymer Desalting Prior To Mass Spectrometry Using 96–Well Solid–Phase Extraction Plates, Abstract No. P9, DNA 2000 International Symposium, Jun. 1–3, 2000. Boston, Mass.

Braman et al. Simple Purification of DNA from Plasmid Minipreps, PCR Amplifications and Agarose Gels, Strategies 10:84–86 (1999).

Brossette et al. A Program for Selecting DNA Fragments to Detect Mutations by Denaturing Gel Electrophoresis Methods, Nucleic Acids Res., 22:4321–4325, (1994).

Gioradano et al. Identification by Denaturing High–Performance Liquid Chromatography of Numerous Polymorphisms in a Candidate Region for Multiple Sclerosis Susceptibility, Genomics, 56:247–253, (1999).

Gross et al. A Comparison of BRCA1 Mutation Analysis by Direct Sequencing, SSCP and DHPLC, Hum. Genet., 105:72–78, (1999).

*Primary Examiner*—James O. Wilson
*Assistant Examiner*—Patrick Lewis

(57) ABSTRACT

A batch process for obtaining polynucleotide fragments, such as dsDNA, having a selected size from a mixture of polynucleotide fragments including the steps of a) applying a solution of the mixture of polynucleotide fragments and a counterion agent to a binding medium having a hydrophobic surface; b) contacting the binding medium with a first stripping solvent and counterion agent, the first stripping solvent having a concentration of organic component sufficient to release from the binding medium all polynucleotide fragments having a size smaller than the selected size, and removing the first stripping solvent from the binding medium; and c) contacting the binding medium with a second stripping solvent having a concentration of organic component sufficient to release from the binding medium the polynucleotide fragments having the selected size, and removing the second stripping solvent from the binding medium. The binding medium can be organic polymer or inorganic particle beads. The mixture of polynucleotides can be the product of a PCR amplification. The binding medium can be contained within a column, a web or a container.

11 Claims, 3 Drawing Sheets

U.S. PATENT DOCUMENTS

| | | | |
|---|---|---|---|
| 5,616,701 A | 4/1997 | Woodard et al. | 536/25.4 |
| 5,651,931 A | 7/1997 | Bailey | |
| 5,705,628 A | 1/1998 | Hawkins | 536/25.4 |
| 5,772,889 A | 6/1998 | Gjerde | |
| 5,783,686 A | 7/1998 | Gonzales | 536/25.4 |
| 5,795,976 A | 8/1998 | Oefner | |
| 5,808,041 A | 9/1998 | Padhye | |
| 5,837,520 A | 11/1998 | Shabram | |
| 5,942,610 A | 8/1999 | Nelson | |
| 5,969,228 A | 10/1999 | Gorstein | 73/23.22 |
| 5,972,222 A | 10/1999 | Gjerde | |
| 5,986,085 A | 11/1999 | Gjerde | |
| 5,997,742 A | 12/1999 | Gjerde | |
| 5,998,604 A | 12/1999 | Fearon | |
| 6,017,457 A | 1/2000 | Gjerde | |
| 6,024,878 A | 2/2000 | Gjerde | |
| 6,056,877 A | 5/2000 | Gjerde | |
| 6,066,258 A | 5/2000 | Gjerde | |
| 6,090,558 A | 7/2000 | Butler | |
| 6,120,985 A | 9/2000 | Laugharn, Jr. | |
| 6,156,206 A | 12/2000 | Gjerde | |
| 6,174,441 B1 | 1/2001 | Gjerde | |
| 6,177,559 B1 * | 1/2001 | Gjerde et al. | |
| 6,258,264 B1 | 7/2001 | Gjerde | |
| 6,265,168 B1 * | 7/2001 | Gjerde et al. | |
| 6,419,824 B1 | 7/2002 | Gjerde et al. | |
| 6,471,866 B1 | 10/2002 | Gjerde et al. | |
| 6,475,388 B1 | 11/2002 | Gjerde et al. | |

FOREIGN PATENT DOCUMENTS

| | | | |
|---|---|---|---|
| WO | 94/11305 | 5/1994 | C02F/1/28 |
| WO | 98/40395 | 9/1998 | C07H/21/04 |
| WO | 98/48913 | 11/1998 | B01D/15/00 |
| WO | 98/48914 | 11/1998 | B01D/15/08 |
| WO | 98/56797 | 12/1998 | C07H/1/00 |
| WO | 99/19514 | 4/1999 | C12Q/1/68 |

OTHER PUBLICATIONS

Huber et al. High–Resolution Liquid Chromatography of DNA Fragments on Non–Porous Poly (Styrene–Divinylbenzene Particles), Nucleic Acids Research, vol. 21, No. 5, 1061–1066, 1993.

Huber et al. High–Resolution Liquid Chromatography of Oligonucleotides on Nonporous Alkylated Styrene–Divinylbenzene Copolymers, Analytical Biochemistry, 212, 351–358, (1993).

Huber, Christian High–Performance Liquid Chromatographic Separation of Detritylated Oligonucleotides on Highly Cross–Linked Poly (Styrene–Divinylbenzene) Particles, Journal of Chromatography, 599, 113–118, (1992).

Jones et al. Optimal Temperature Selection for Mutation Detection by Denaturing HPLC and Comparison to Single–Stranded Conformation Polymorphism and Heteroduplex Analysis, Clinical Chem., 45–48, 1999.

Oefner et al. High–Resolution Liquid Chromatography of Fluorescent Dye–Labeled Nucleic Acids, Analytical Biochemistry, 223, 001–008, (1994).

Oefner et al, High Resolution Liquid Chromatography of Nucleic Acids, American Laboratory, 28C–28J, (1994).

Oefner et al. DNA Mutation detection Using Denaturing High–Performance Liquid Chromatography (DHPLC), Current Protocols in Human Genetics, 7.10.1–7.10.12, 1998.

Marlowe et al. A Method for Detection and Quantitation of PCR Template in Environmental, Samples by High Performance Liquid Chromatography, Journal of Microbiological Methods, 28 (1997) 45–53.

Sauer et al. Fast and Efficent Enzyme Removal with QIAquick™Spin Kits, Qiagen News 5:13–15 (1998).

Millipore Corporation, Data Sheet—ZipTip™ Pipette Tips for Sample Preparation, http//:www.millipore.com (Aug. 1, 2000).

Millipore Corporation, Protocol–Sample Preparation of Oligonucleotides Prior to MALDI–TOF MS Using Zip Tip C18 and ZipTip $\mu$–C18 Pipettes Tips, http//:www.millipore.com/analytical/pubdbase.nsflTN225.html(Aug. 1, 2000).

All–Chrom Newsletter Metal Components, A Potential Source of Interference in HPLC Analysis, Alltech–Applied Science vol. 25, No. 1, pp. 1–6, Jun., 1986.

Coenen et al. Optimization of the Separation of the PR and SP Diasteromers of Phosphate–Methylated DNA and RNA Dinuleotides, Journal of Chromatography, 596, 59–66, (1992) .

DNA Cleanup and Gel Extraction, Qiagen Product Guide, pp. 169–176, 1999.

Drager et al. High–Performance Anion–Exchange Chromatpgraphy of Oligonucleotides, Analytical Biochemistry, 145, 47–56 (1985).

Edge Biosystems, Research Products Handbook, p. 4, 1999–2000.

Fritz et al. High–Perofrmance Liquid Chromatography in Polynucleotide Synthesis, Biochemistry. 17, 7, pp. 1257–1267, (1978).

Furst et al. Simultaneous Determination of Myocardial Nucleotides, Nucleosides, Purine Bases and Creatine Phosphate by Ion–Pair High–Performance Liquid Chrmatography, J. Chromatography, 578, 39–44, Jul. 1, 1992.

Green et al, HPLC Purification of Synthetic Oligodeonyribonucleotides Contatining Base– and Backbone–Modified Sequences, BioTechniques 19:5, pp. 836–841 (Nov. 1993).

Green et al. Preparative Purification F Sypercoiled Plasmid DNA for Therapeutic Applications, BioPharm, 10:5 pp. 52–62, May 1997.

Heftman, Chromatography, 5th Edition, Journalof Chromatography Library—Vol. 51A. Elsevier, pp. A299–A300 1992.

Huang et al. Large–Scale Purification of Synthetic Oligonucleotides and Carcinogen–Modified Oligodeoxynucleotides on a Revers–Phase Polystyrene (PRP–1) Column, Analytical Biochemsitry, 190, 21–25, 1990.

Ip et al. Separation O Nucleosides and Nucleotides by Reversed–Phase HPLC with Volatile Buffers Allowing Sample Recovery, Analytical Biochemistry, 147, 180–185, (1985).

Kwiatkowski et al. Use of RP Ion Pair Chromatography to Fractionate and Purify DNA Fragments and Monomeric Components of RNA, Acta Chemica scandinavica B. 38, 9, 721–733, (1984).

Moriyama et al. New RP HPLC Column For Oligonucleotide Separtion, Journal of Chromatography, 445, 225–233, (1988).

Nucleic Acid Purification and Labeling, Promega Life Science Catalog, p. 9.10, 1999.

Schmitter et al. Rapid Purification of DNA Fragments by High–Performance Size–Exclusion Chromatography, J of Chrom. (1986) 378:462–466.

Stratagene Catalog, pp. 114–115, 1999.

Tashlitskii et al. Optimization of Conditions for Ion–Pair HPLC of Oligonulceotides Bioorg. Khim., 23 (9), 732–741 (1997) Biosis Abstract No. 01070821.

Vtorushna et al. Study of Diastereomers of Non–Ionic Oligonucleotide Analogues. VI. Separation of Diastereomers of Ethyl Phosphotriesters O Octanucleotide d(GC-CAAACA) By Means of HP Complementary Chromatography, Bioorg. Khim. 18.1. 92–99 (1992).

*Dizdaroglu et al., "Separation of small DNA and RNA oligonucleotides by high performance anion exchange liquid chromatography", Journal of Chromatography, vol. 171, pp. 321–330, Apr. 1979.*

Zon et al. in High Performance Liquid Chromatography in Biotechnology, Hancock ed., John Wiley & sons, New York (1990) pp. 301–398.

Kwiatkowski, M., Use of Reverse Phase Ion Pair Chromatography to Fractionate and Purify DNA Fragments and Monomeric Components of RNA, Acta Chemica Scandinavica, vol. B 38, 721–733(1984).

Georgopoulos, D.E., Use of High–Performance Liquid Chromatographic Fractionation of Large RNA Molecules in the Assay of Group I Intron Ribozyme Activity, Journal of Chromatography A, vol. 868, 109–114(2000).

Garcia, S., Behaviour of Macromolecular RNA in Reversed– Phase HPLC, Journal of Chromatographic Science, vol. 21, 398–404 (1983).

Djordjevic, N., HPLC Separation of Oligonucleotides in Isocratic and Temperature–Programming Mode, Analytical Chemistry, vol. 70 No. 9, 1921–1925(1998).

Dolezal, M., Micropreparative Separation of Transfer Ribonucleic Acids by High–Performance Liquid Chromatography, Journal of Chromatography, vol. 463, 409–417 (1989).

Bischoff, R., Isolation of Specific tRNAs Using an Ionic–Hydrophobic Mixed–Mode Chromatographic Matrix, Analytical Chemistry, vol. 151, 526–533(1985).

Haupt, W., Comparison of Several High–Performance Liquid Chromatography Techniques for the Separation of Oligodeoxynucleotides According to Their Chain Lenghths, Journal of Chromatography, vol. 260, 419–427(1983).

Oligotex Handbook (Jul. 1999), pp. 18–27.

Oligotex RNeasy Midi/Maxi Handbook (Oct. 1999), pp. 20–30.

Qiagen QIAvac Handbook (Apr. 1999), pp. 19–22.

Qiagne RNA/DNA Handbook (Nov. 1998), pp. 18–23, 51–52.

Yang, D.Y., Technical Note: Improved DNA Extraction From Ancient Bones Using Silica–Based Spin Columns, American Journal of Physical Anthropology, vol. 105, 539–543(1988).

Webster, K.R., A Rapid Method for Purification of Synthetic Oligoribonucleotides, Bio Techniques, vol. 11 No. 5, 658–661(1991).

Antia, F.D., High–Performance Liquid Chromatography at Elevated Temperatures: Examination of Conditions for the Rapid Separation of Large Molecules, Journal of Chromatography, vol. 435, 1–15(1988).

Millipore Corporation, Technical Note: TN225, Mar. 30, 2000.

Huber, C.G., A Comparison of Micropellicular Anion–Exchange and Reversed–Phase Stationary Phase for HPLC Analysis of Oligonucleotides, LC–GC, vol. 14 No. 2, 114–127(1996).

Roughi, A.M., Chromatography, Mass Spectrometry, C&EN Washington, 46–48, Mar. 16, 1998.

U.S. patent application Ser. No. 09/809,867, filed Mar. 15, 2001, pending.

U.S. patent application Ser. No. 09/753,856, filed Jan. 2, 2001, pending.

* cited by examiner

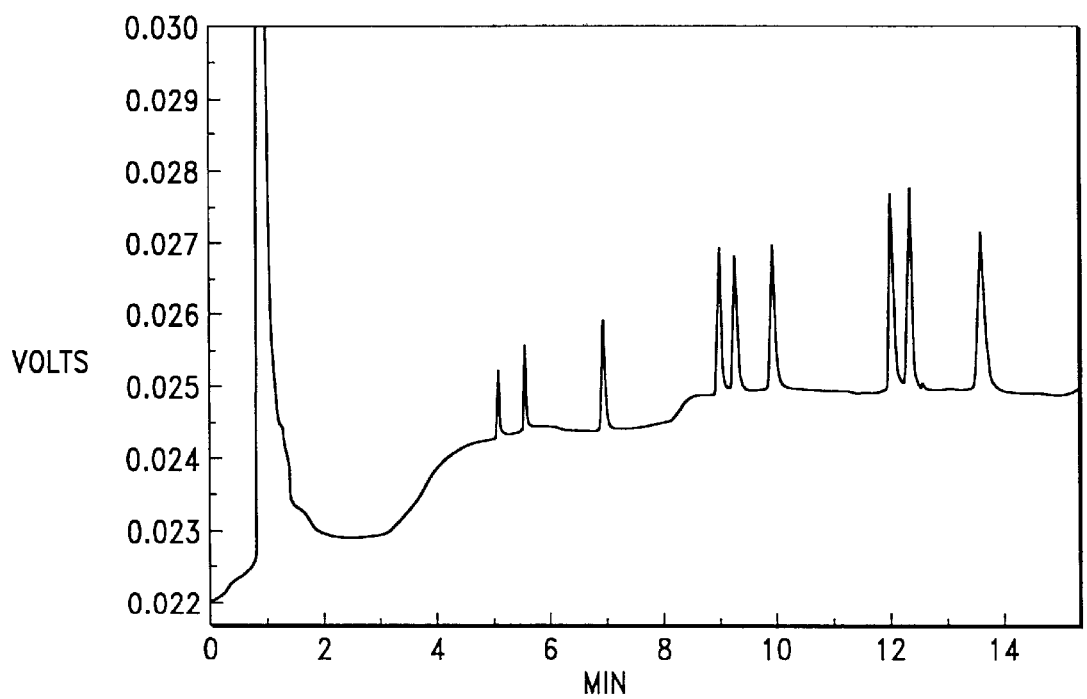
*FIG.—3*
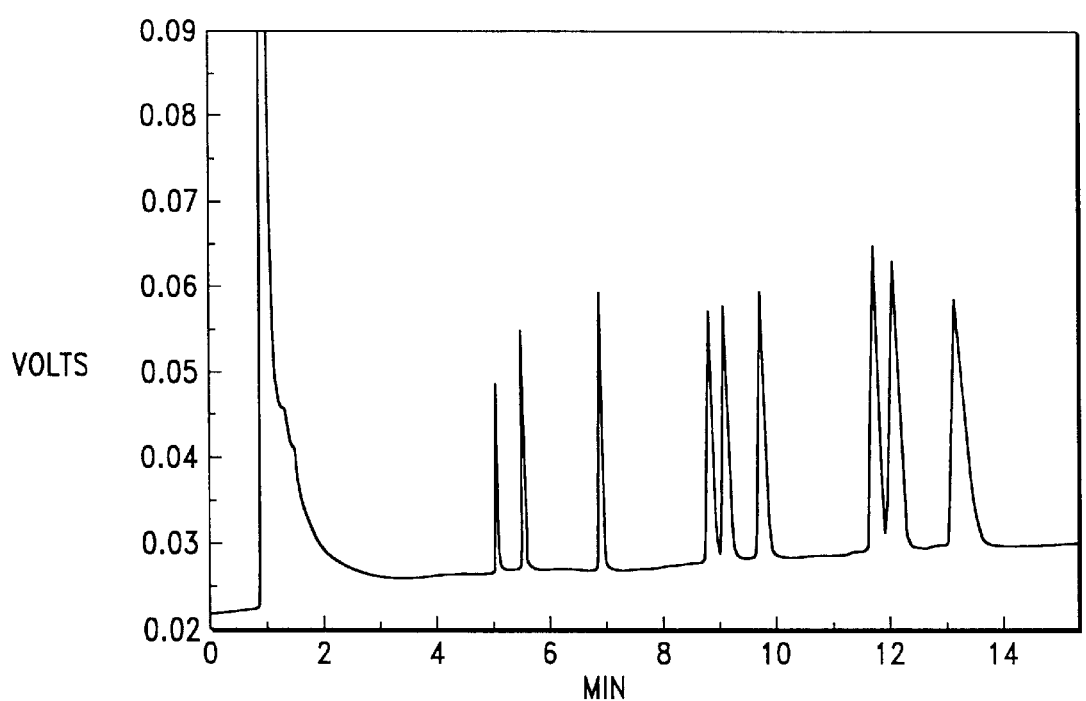
*FIG.—4*

US 6,642,374 B2

PROCESS FOR SEPARATION OF POLYNUCLEOTIDE FRAGMENTS

CROSS REFERENCE TO RELATED COPENDING APPLICATIONS

This application is a Continuation of co-pending, commonly assigned patent application Ser. No. 09/391,963 filed Sep. 8, 1999 (U.S. Pat. No. 6,177,559) which is continuation of Ser. No. 09/065,913 filed Apr. 24, 1998 (U.S. Pat. No. 5,986,085) which claims benefit to 60/044,856 filed Apr. 25, 1997.

FIELD OF THE INVENTION

The invention pertains to the field of isolation and purification of polynucleotides. In particular, the invention relates to a process for purification of polynucleotides.

BACKGROUND OF THE INVENTION

The separation and quantification of polynucleotides such as DNA is of critical importance in molecular biology and improved methods are a focus of current interest. One separation method includes size-exclusion chromatography (E. Heftmann, in *J. Chromatog. Lib.*, Vol. 51A, p. A299 (1992)). The disadvantages of this method include low resolution and low capacity. Another separation method is anion exchange chromatography of DNA with tetramethylammonium chloride containing mobile phases as described in European patent application 0 507 591 A2 to Bloch. However, the separation is not strictly size-based, and the resolution is not always adequate. A further disadvantage of methods which rely on binding of anionic DNA includes the required use of high concentrations of nonvolatile salts in the mobile phase; this interferes with subsequent isolation and measurement (e.g. mass spectral analysis) on the separated fragments.

Thus there is a need in the art for a size-based separation process for DNA which has high capacity and resolution, and which does not require use of nonvolatile salts.

SUMMARY OF THE INVENTION

Briefly, the instant invention comprises a process for non-specifically binding all of the fragments in a polynucleotide mixture onto a solid binding medium having a hydrophobic surface in the presence of a counterion agent, and the selective release of the fragments based on their size, from smallest to largest, as the concentration of the organic component of the mobile phase is increased. In one embodiment, the binding medium is comprised of beads having a hydrophobic surface. The process does not require use of a high pressure liquid chromatography (HPLC) system and is amenable to scale up or miniaturization.

Accordingly, one aspect of the present invention provides a process for separating a mixture of polynucleotides which is based on the base-pair length of the fragments.

As another aspect of the present invention, there is provided a separation process for a mixture of polynucleotides which can be carried out using binding medium incorporated into a variety of separation configurations including a container such as a column or well.

In another aspect, the present invention provides a separation process for a mixture of polynucleotides which utilizes a hydrophobic binding medium enmeshed in an inert fiber matrix.

In yet another aspect, the present invention provides a simple, inexpensive, and rapid process for separating a mixture of polynucleotide fragments.

In a further aspect, the present invention provides a separation process for polynucleotide fragments which does not require the use of nonvolatile salts.

One embodiment of the instant invention is directed to a batch process for obtaining polynucleotide fragments (such as dsDNA polynucleotides) having a selected size from a mixture of polynucleotide fragments, comprising the steps of (a) applying a solution of the mixture of polynucleotide fragments and a counterion agent to a binding medium having a hydrophobic surface;

(b) contacting the binding medium with a first stripping solvent and counterion agent, the first stripping solvent having a concentration of organic component, such as acetonitrile, sufficient to release from the binding medium all polynucleotide fragments having a size smaller than the selected size, and removing the first stripping solvent from the binding medium; and (c) contacting the binding medium with a second stripping solvent having a concentration of organic component sufficient to release from the binding medium the polynucleotide fragments having the selected size, and removing the second stripping solvent from the binding medium.

The binding medium can be rinsed with fresh first stripping solvent following step (b) to remove residual fragments having a size smaller than the selected size therefrom. The binding medium can also be rinsed with fresh second stripping solvent following step (c) to remove residual polynucleotide fragments of the selected size therefrom. The counterion agent preferably is triethylammonium acetate or triethylammonium hexafluoroisopropyl alcohol. The binding medium is preferably porous or nonporous beads having a diameter of from about 1.0 to 1,000 $\mu$m. The beads can consist of organic polymer such as a copolymer of vinyl aromatic monomers selected from the group consisting of styrene, alkyl substituted styrene, alpha-methylstyrene and alpha substituted alpha-methylstyrene. Alternatively, the beads can comprise inorganic particles such as silica, silica carbide, silica nitrite, titanium oxide, aluminum oxide, zirconium oxide modified to have a hydrophobic surface. The hydrophobic surface can be an organic polymer supported on the inorganic particle. The hydrophobic surface can be long chain hydrocarbons having from 8–24 carbons bonded to the inorganic particle. Preferably, any residual polar groups of the inorganic particle have been end-capped with trimethylsilyl chloride or hexamethyldisilazane.

The process of the invention is particulary useful in separating the products of a PCR amplification.

The binding medium can be contained within a column, a web or a container. In one embodiment, the medium (such as beads) is contained within a web consisting of an inert fiber matrix and beads enmeshed in the matrix. In a preferred embodiment, the binding medium consists of hydrophobic beads which are contained a polymeric (such as polytetrafluoroethylene) fibril matrix with the ratio of beads to fibril matrix being in the range of 29:1 to 4:1 by weight.

Other aspects and advantages of the present invention are described further in the following detailed description.

BRIEF DESCRIPTION OF THE DRAWINGS

FIG. 3 is a separation of pUC18-DNA HaeIII digest on a column packed with a nonporous poly(styrene-divinylbenzene) polymer beads. The column dimensions were 50 mm×6.5 mm i.d.

FIG. 4 is a separation of pUC18-DNA HaeIII digest (20 times more sample was injected as compared to FIG. 3) on a column packed with a nonporous poly(styrene-divinylbenzene) polymer beads. The column dimensions were 50 mm×6.5 mm i.d.

DETAILED DESCRIPTION OF THE INVENTION

Figure 1:
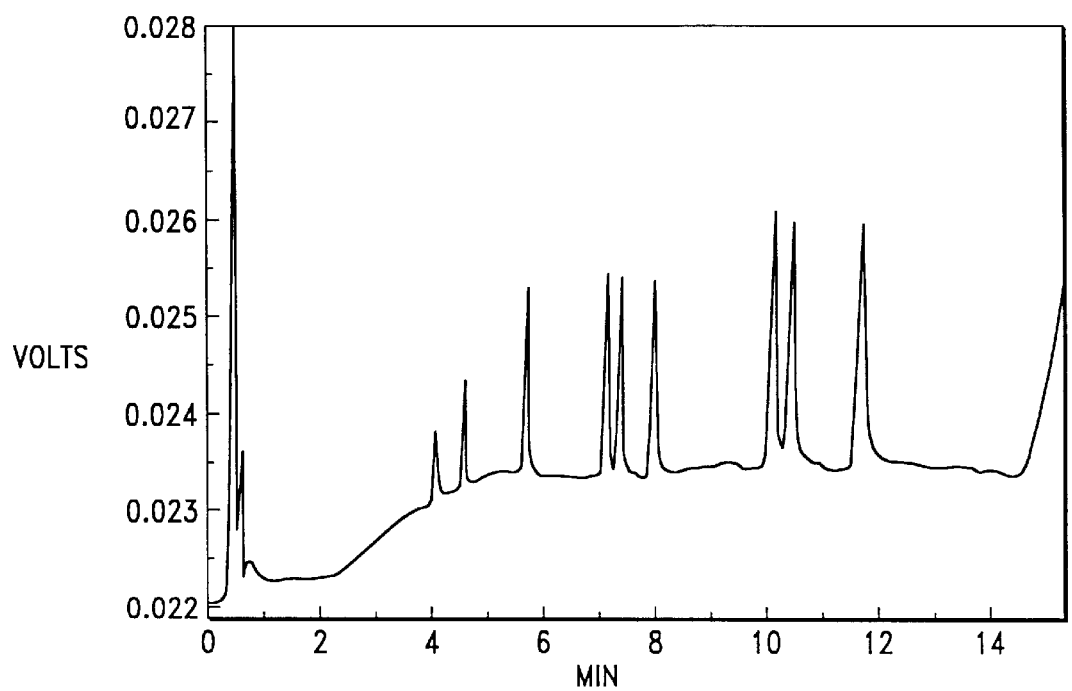
FIG. 1 is a separation of pUC18-DNA HaeIII digest on a column packed with a nonporous poly(styrene-divinylbenzene) polymer beads. The column dimensions were 30 mm×4.6 mm i.d.

The term "polynucleotide" is defined as a linear polymer containing an indefinite number of nucleotides, linked from one ribose (or deoxyribose) to another via phosphoric residues. The present invention can be used in the separation of RNA or of double- or single-stranded DNA or of synthetic DNA analogs. The polynucleotide can be a linear molecule or a closed circle and can be modified, e.g. labeled with biotin or fluorescent molecules. For purposes of simplifying the description of the invention, and not by way of limitation, the separation of double-stranded DNA will be described in the examples herein, it being understood that all polynucleotides are intended to be included within the scope of this invention.

A "counterion agent" is a compound used to form a neutral salt with anionic DNA. Counterion agents that are volatile, such as trialkylammonium acetate and trialkylammonium carbonate, are preferred for use in the method of the invention, with triethylammonium acetate (TEAA) and triethylammonium hexafluoroisopropyl alcohol being most preferred.

"Non-specific binding" refers to binding to all of the DNA fragments in a mixture despite differences in the DNA sequence or size of the different DNA molecules. In the present invention, such binding occurs when the fragments are exposed to the hydrophobic surface of a binding medium in a stripping solvent containing a counterion agent but lacking organic component or at low concentrations of organic component.

"Binding medium" refers to a solid phase having a hydrophobic surface suitable for binding DNA fragments in the presence of an aqueous phase containing a counterion agent. Examples include beads or particles.

"Organic component" refers to a water-soluble organic solvent which is suitable for use in an aqueous solution in the present invention for releasing polynucleotides from the hydrophobic surface of the binding medium.

"Stripping solvent" refers to an aqueous solution containing an organic component for use in the present invention for releasing polynucleotides from the hydrophobic surface of the binding medium.

"Organic component" refers to a water-soluble organic solvent which is suitable for use in the stripping solvent of the present invention.

As demonstrated by Bonn et al. in U.S. Pat. No. 5,585,236, use of hydrophobic beads in HPLC gave size-based separation of polynucleotides. In the presence of a counterion agent, polynucleotides eluted in the order of smallest to largest as the concentration of the organic component of the mobile phase was increased.

In traditional reverse-phase HPLC separations, variations in the length of the column alter the elution profile of the analyte due to partitioning of the analyte between the stationary phase and the mobile phase. As will be demonstrated hereinbelow, applicants have discovered that when hydrophobic beads were used as the separation medium of a HPLC column, no change in the elution profile of polynucleotide fragments was observed with a change in the length of the separation column. Applicants have discovered that size-based separation of polynucleotides can also be achieved using a variety of hydrophobic binding media without using HPLC systems. This makes possible processes for separations of polynucleotides not heretofore known in the art.

In U.S. Pat. No. 5,585,236, Bonn et al. had characterized the polynucleotide separation process as reverse phase ion pairing chromatography (RPIPC). However, since RPIPC does not incorporate certain essential characteristics described in the present invention, another term, Matched Ion Polynucleotide Chromatography (MIPC), has been selected. MIPC as used herein, is defined as a process for separating single and double stranded polynucleotides using non-polar beads, wherein the process uses a counterion agent, and a stripping solvent to release selected polynucleotide fragments from the beads.

The present invention is a process for binding DNA non-specifically and reversibly in the presence of a counterion to a solid phase binding medium, such as beads, having a hydrophobic surface. In the process of the invention, the DNA can be present in solution with water or in a reaction buffer. Such a solution can also contain other components, such as other biomolecules, inorganic compounds and organic compounds as long as such other components do not interfere significantly with the binding process of the invention. As an example, the solution can be a reaction product of a PCR amplification, and the process of the present invention can be used to separate impurities, such as primers or primer dimers, from the amplified sequence.

The present invention requires a counterion agent for forming a hydrophobic salt with anionic DNA to enable the hydrophobic interaction of the DNA-counterion with the binding medium. Counterion agents that are volatile, such as trialkylammonium acetate and trialkylammonium carbonate, are preferred for use in the process of the invention, with triethylammonium acetate (TEAA) and triethylammonium hexafluoroisopropyl alcohol being most preferred. Trialkylammonium phosphate can also be used. The counterion agent can be added to the DNA mixture first or the DNA mixture can be injected into a polar stripping solvent containing the counterion agent. Preferred counterion agents are those which are easily removed after the separation process.

The present invention utilizes an aqueous stripping solvent containing organic component. At increasing concentrations of the organic component in the stripping solvent, DNA fragments can be released from the binding medium as a function of the size of the fragments, from smallest to largest. Preferred stripping solvents must be able to both release the DNA-counterion from the surface and maintain the DNA-counterion in solution. Preferred stripping solvents do not interfere with the isolation or recovery of the fragments and are easily removed after the separation. The solvent is preferably selected from the group consisting of alcohols, nitriles, dimethylformamide, esters, and ethers. Examples of suitable solvents include acetonitrile, alcohols, 2-propanol, methanol, tetrahydrofuran, and 1,4 dioxane. The concentration of organic component and counterion agent required for a separation will depend on the binding medium used, and the conditions are optimized by routine methods.

In the process of the present invention, the release of the fragments from the surface can be modulated by exposing the surface of the binding medium to variations in parameters such as temperature and pH. The release of fragments can also be modulated by chemical interactions, such as the use of an additive, e.g. a second, more polar counterion agent, in the stripping solvent that would competitively form a stable complex with the DNA-counterion fragments, and would be able to release the fragments from the surface of the medium, The fragments in solution can be detected by any suitable method such as by UV absorbance or other means (e.g. fluorescence, radioactivity).

The process of the present invention requires a solid phase binding medium having a suitable surface for binding the DNA-counterion. In a preferred embodiment, the medium comprises separation beads or particles. A wide variety of surface chemistries can be used in the present invention, but the preferred bead surface is hydrophobic. The preferred surface does not contribute to competing mechanisms, ex. anion exchange or size-exclusion, and preferably does not hinder binding or release of the DNA-counterion by steric or energetic interfering factors.

Examples of suitable beads for use in the present invention include polymer beads as described in copending U.S. patent application Ser. No. 09/058,580, filed on Apr. 10, 1998 (abandoned), and coated inorganic particles as described in copending U.S. patent application Ser. No. 09/058,337, filed on Apr. 10, 1998 (abandoned).

Chromatographic efficiency of the beads is predominantly influenced by the properties of surface and near-surface areas. The main body or the center of such beads can exhibit entirely different chemistries and physical properties from those observed at or near the surface of the beads.

An example of a suitable bead is a porous or nonporous polymer bead comprised of a copolymer of vinyl aromatic monomers. Examples of vinyl aromatic monomers include styrene, alkyl substituted styrene, alpha-methylstyrene, and alkyl substituted alpha-methylstyrene.

Another example of a suitable bead is a porous or non-porous particle such as silica, silica carbide, silica nitrite, titanium oxide, aluminum oxide, zirconium oxide which is modified to have a hydrophobic surface. The hydrophobic surface can be an organic polymer supported on the inorganic particle. In one embodiment, the hydrophobic surface includes long chain hydrocarbons having from 8–24 carbons bonded to the inorganic oxide particle. An example is a silica particle having substantially all surface substrate groups reacted with a hydrocarbon group and then endcapped with a non-polar hydrocarbon or substituted hydrocarbon group, preferably a tri(lower alkyl)chlorosilane or tetra(lower alkyl)dichlorodisilazane. The particle can be end-capped with trimethylsilyl chloride or hexamethyldisilazane.

Beads useful in the present process can be a variety of shapes, which can be regular or irregular; preferably the shape maximizes the surface area of the beads. The beads should be of such a size that their separation from solution, for example by filtration or centrifugation, is not difficult.

Figure 2:
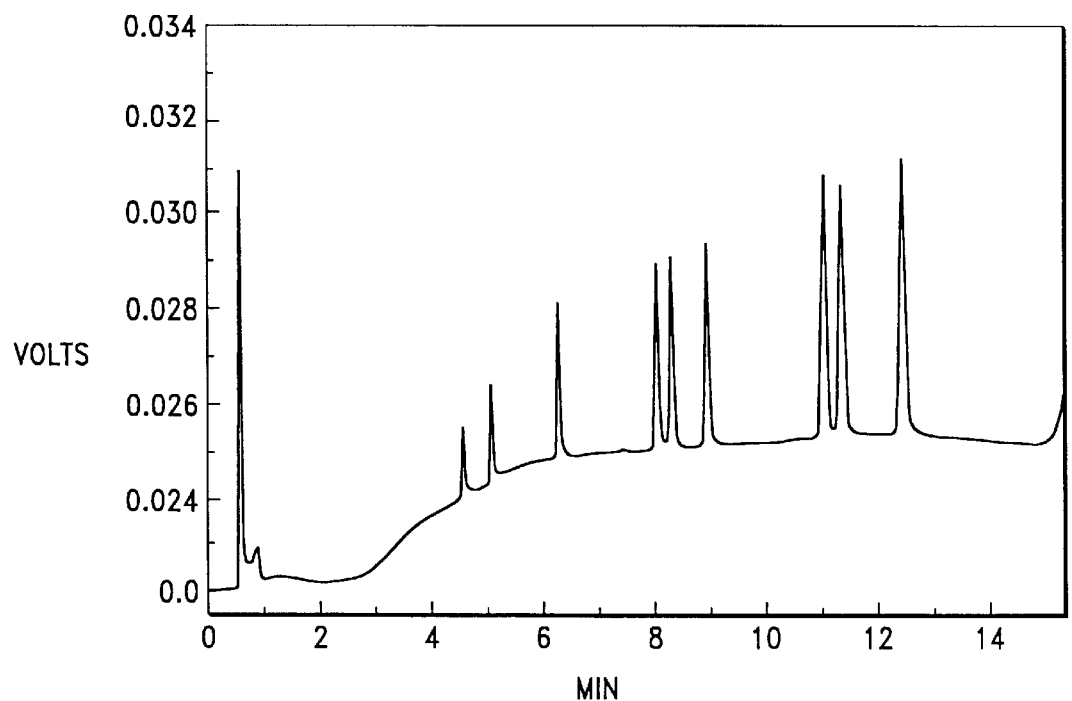
FIG. 2 is a separation of pUC18-DNA HaeIII digest on a column packed with a nonporous poly(styrene-divinylbenzene) polymer beads. The column dimensions were 50 mm×4.6 mm i.d.

In one embodiment, the beads of the present invention have a diameter of about 1 to 100 $\mu$m and can be used in an HPLC system. In traditional reverse-phase HPLC separations, variation in the length of the column alters the elution profile of the analyte due to partitioning of the analyte between the stationary phase and the stripping solvent. For a given sample, differences in selectivity and resolution will be observed when the column length is changed. It has now been surprisingly discovered by applicants that this is not the case for DNA separations on hydrophobic beads as described herein and this observation is the basis for the process of the present invention. This phenomenon is illustrated by the separations described in FIGS. 1 and 2. Referring to FIG. 1, a DNA mixture was separated as described in EXAMPLE 1. It can be seen that the separation profiles were very similar. Shorter columns can be used without diminishing the resolution, which would have the advantages of lower back-pressure, good flow paths with small extra column effects. In addition, peak broadening would be reduced in shorter columns due to less diffusion of the solutes. It was also observed that the capacity of the column could be increased by increasing the diameter of the column without a decrease in separation performance, as shown in FIGS. 2 and 3. In FIG. 3, the separation conditions were the same as for FIG. 2 except that a column having a wider bore was used.

As described in EXAMPLE 2, in an experiment to assess the capacity of the nonporous polymer beads, FIG. 4 shows a separation using the same conditions as for FIG. 3, but after injecting a sample having about 20-fold more DNA. The increase in sample loading did not have a significant effect on the separation performance. The capacity of the beads used in EXAMPLES 1 and 2 was about 10 $\mu$g DNA per gram of beads.

Figure 5:
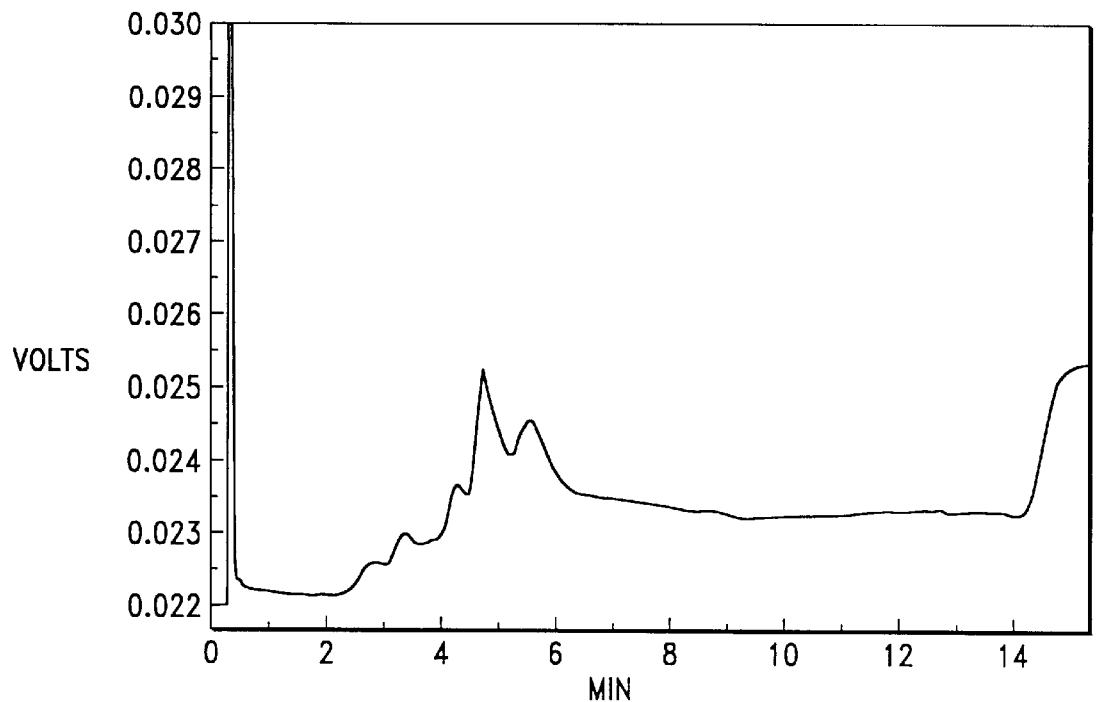
FIG. 5 is a separation of pUC18-DNA HaeIII digest on two discs containing binding media placed in series and containing nonporous poly(styrene-divinylbenzene) polymer beads. The dimensions of each disc was 0.7 mm×4.6 mm i.d.

Referring to FIG. 5 and EXAMPLE 4, a DNA fragment separation was performed using discs of 0.7 mm thickness, and demonstrated that separation is possible using a thin separation bed containing hydrophobic binding medium. The resolution is adequate for some applications such as cleanup of the product of a PCR amplification.

An example would be the separation of a PCR product from residual primers, dNTP material, and primer dimers. Primer dimers form when the two primers associate with a 2 to 3 base pair overlap and are often a byproduct of the PCR reaction. These dimers form when the two primers associate, e.g. with a 2 to 3 base pair overlap. These dimers are approximately the size of the two primers less 1 to 3 base pairs. Since primer dimers are double stranded, they are particularly difficult to remove from PCR products, but are readily resolved using the process of the present invention as demonstrated in EXAMPLE 5.

The geometry and configuration of the container supporting the binding medium can be varied without loss of the ability to separate DNA fragments by size. For example, purification of large-scale DNA mixtures is possible, and could be used as a preparative step in obtaining pharmaceutical grade polynucleotides.

In one embodiment of the process of the present invention, the separation can be conducted as a batch process in a container. The volume of the container can vary widely depending on the amount of mixture to be separated. The container can be a column, a flask, a well, or a tank, for example. The size of such a container can be as small as a well on a 96-well microtiter plate or as large as a multi-liter vat, for example. The binding medium can be beads. Beads useful in the batch process can be a variety of shapes, which can be regular or irregular; preferably the shape maximizes the surface area of the beads. The beads should be of such a size that their separation from solution, for example by filtration or centrifugation, is not difficult.

In one example, the DNA mixture, counterion, and beads are mixed in bulk with a polar solution in a container, and binding is allowed to occur. Preferably, all of the DNA-counterion will bind nonspecifically to the beads under the initial conditions in which the stripping solvent has low concentration of organic component. To release DNA fragments from the beads, the beads are brought into contact with a stripping solvent of sufficient concentration of organic component. Elution conditions for DNA fragments having a selected base-pair length can be predetermined, e.g. by determining the elution profile of a standard DNA mixture at various concentrations of stripping solvent. This calibration procedure can be conducted on a small scale and applied to a large-scale process. Specific stripping solvent compositions can be adjusted to elute polynucleotide fragments of any specific base pair size. An example of the high resolution which can be obtained in a single equlibria bulk process is exemplified by referring to FIG. 6 and EXAMPLE 3 where isolation of a 102 base pair fragment was achieved by incrementally increasing the ACN concentration from 14.6% to 15.9%.

In a preferred embodiment of the process of the invention, after the sample mixture is bound, stripping solvent is applied in a first release step in which the organic component is applied at a concentration which will release fragments smaller than the desired fragment. The beads are then separated from the stripping solvent, e.g. by centrifugation or by filtration. Stripping solvent is then applied to the beads in a second release step in which the stripping solvent is applied at an elevated concentration, e.g. an incrementally elevated concentration, which selectively releases the desired size of fragment. Optionally, the process can be repeated with stripping solvent applied at increasing concentrations of organic component in order to release longer fragments of discrete base pair length. Each fragment can be recovered, e.g. by collecting the stripping solvent at each concentration of organic component. It is possible to have multiple wash steps at a single concentration of stripping solvent to ensure complete removal of the desired size fragment.

In another example of a batch process of the present invention, the separation is performed using a column, e.g. an open column under gravity flow conditions or a low pressure column equipped with a peristaltic pump. The binding medium comprises beads having a diameter large enough to permit flow of stripping solvent without requiring high pressure pumps. Preferred beads have a diameter of about 20 to 1000 microns and can be made from various materials as described hereinabove. The dimensions of the column can range from about 10 cm to 1 m in length, and 1 to 100 cm in diameter, for example. In operation, the column is first conditioned using a polar solvent. A DNA-counterion mixture is applied to the column in a convenient volume such as from 1 to 50 mL. For dilute samples having a large volume, the sample can be applied continuously, or in stages, to "load" the column. Preferably, all of the DNA-counterion will bind to the binding medium under the initial conditions in which the stripping solvent has low concentration of organic component. To release DNA fragments from the separation beads, the beads are brought into contact with a stripping solvent of sufficient concentration of organic component. Elution conditions for a DNA fragment having a selected base-pair length can be predetermined, e.g. by determining the elution profile of a standard DNA mixture at various concentrations of stripping solvent. This calibration procedure can be conducted on a small scale and applied to a large-scale process. Specific stripping solvent compositions can be adjusted to elute polynucleotide fragments of any specific base-pair size in analogy to the bulk equilibria process as described hereinabove. After the sample mixture is bound to the binding medium in the column, stripping solvent is applied in a first release step in which the organic component is present at a concentration which will release fragments smaller than the desired fragment; stripping solvent is then applied in a second release step in which the organic component is present at an elevated concentration, e.g. an incrementally elevated concentration, which selectively releases the desired fragment. Optionally, stripping solvent can be applied in a gradient of increasing concentration of organic component, e.g. a step-gradient or continuous gradient, in order to release longer fragments. By using a step gradient of increasing ACN concentration, larger fragments can be removed in discrete base pair lengths from the separation beads and isolated. Each fragment is recovered, for example, by collecting the stripping solvent at each concentration of organic component. For each fragment, the separation process can be repeated, if necessary, e.g. by application to another column.

In another embodiment of the invention, the binding medium can be retained in a web or pad. An example is a web of inert fiber matrix with hydrophobic binding medium, such as the beads as described hereinabove, enmeshed in the matrix. The web of the present invention is a composite article comprising binding medium which has been incorporated into a fabric or membrane. The term "incorporated into a fabric membrane" means that the binding medium is encapsulated by or trapped within a fabric or membrane, is stabilized within a fabric or membrane or is covalently attached to a fabric or membrane such that the binding medium does not exist as free flowable particulate bulk material and is not separable from the web under liquid chromatography conditions.

When the binding material is incorporated into a web, the web may be woven or non-woven. The spaces between fibers of the web should be small enough to prevent binding medium material from passing through the web. The density of non-woven fibers and the density of warp and weft fibers of the web can be routinely adjusted to provide the desired density and porosity.

The web fibers can be made of any suitable material so long as the material is porous. Suitable materials are described in U.S. Pat. No. 5,338,448 to Gjerde. Generally, the fibers will be made of a porous synthetic or natural polymeric material, e.g. polytetrafluoroethylene, cellulose, polyvinyl chloride, nylon, etc. The DNA in the sample preferably binds only to the binding medium and the binding is not detrimentally affected by the fiber matrix material. When the binding medium consists of polymeric beads, the ratio of beads to fiber matrix material can be in the range of 19:1 to 4:1 by weight, for example.

In one embodiment, the web is mounted on a support and the sample is applied and eluted in a manner analogous to the open column process as described hereinabove. The web material can be packed into a column. An advantage of using a web material is that it provides flexibility in how thin a column bed can be made, e.g. the web can be formed as a disk. Also, several uniform beds can be made at once. Multiple webs can be supported in a row or adapted to a matrix well format, e.g. a 4, 8, 16, or 96 well plate. The web can be used in analogy to the bulk equilibria process or column as described hereinabove with a binding step followed by release steps.

An example of a suitable fibril matrix is polytetrafluoroethylene (PTFE) as described in U.S. Pat. No. 4,906,378 to Hagen. The ratio of beads to PTFE fibril matrix can be in the range of 19:1 to 4:1 by weight, for example.

The process of the invention preferably includes precautions to prevent contamination with multivalent cations such as Fe(III), Cr(III), or colloidal metal contaminants. Multivalent cations can cause non-specific binding of the DNA to the surfaces of conduits and containers which can lead to low recovery. The inner surfaces, which contact liquids within the system, preferably are treated to remove multivalent contaminants, e.g. treating with an acid such as nitric acid. The efficiency of the separation process may be enhanced by the optional addition of a chelating agent such as EDTA, e.g. at a concentration of 0 to 0.1 M. Suitable precautions are described in copending U.S. patent application Ser. No. 08/748,376 filed Nov. 13, 1996 (now U.S. Pat No. 5,772,889). Precautions can also be taken during the manufacture of the binding medium to prevent contamination with multivalent cations. Examples of suitable precautions in the manufacture of beads, for example, are described in copending U.S. patent application Ser. No. 09/058,580, filed on Apr. 10, 1998, and in copending U.S. patent application Ser. No. 09/058,337, filed on Apr. 10, 1998.

Other features of the invention will become apparent in the course of the following descriptions of exemplary embodiments which are given for illustration of the invention and are not intended to be limiting thereof.

All references cited herein are hereby incorporated by reference in their entirety.

Procedures described in the past tense in the examples below have been carried out in the laboratory. Procedures described in the present tense have not been carried out in the laboratory, and are constructively reduced to practice with the filing of this application.

EXAMPLE 1

Effect of Column Dimensions on the HPLC Separation of DNA Fragments

In the separation shown in FIG. 1, the HPLC column was packed with 2.1 micron C-18 alkylated nonporous poly (styrene-divinylbenzene) polymer beads and a DNA separation was run under the following conditions: Column: 30×4.6 mm i.d.; stripping solvent 0.1 M TEAA, pH 7.2; gradient: 35–55% acetonitrile (ACN) in 3 min, 55–65% ACN in 7 min, 65% ACN for 2.5 min; 100% ACN for 1.5 min, back to 35% ACN in 2 min. The flow rate was 0.75 mL/min, p=1300 psi, detection UV at 260 nm, column temp. 51° C. The sample was 3 µL (=0.12 µg pUC18 DNA-HaeIII digest). For comparison, FIG. 2 shows a separation using a longer column packed with the same sized beads under similar elution conditions: Column: 50×4.6 mm i.d.; stripping solvent 0.1 M TEAA, pH 7.2; gradient: 35–55% ACN in 3 min, 55–65% ACN in 7 min, 65% ACN for 2.5 min; 100% ACN for 1.5 min, back to 35% ACN in 2 min. The flow rate was 0.75 mL/min, p=1650 psi, detection UV at 260 nm, column temp. 51° C. The sample was 5 µL (=0.2 µg pUC18 DNA-HaeIII digest). In FIG. 3, the separation conditions were similar to those of FIG. 2 except that a column having a wider bore diameter was used: the column was 50 mm×6.5 mm i.d. column, temp.=50° C., p=750 psi. The sample was 5 µL (=0.2 µg pUC18 DNA-HaeIII digest).

EXAMPLE 2

Effect of Sample Size on HPLC Separation of DNA Fragments

In an experiment to assess the effect of sample size on the separation, FIG. 4 shows a separation using the same conditions as for FIG. 3, but after injecting a sample having about 20-fold more DNA (4.1 µg pUC18 DNA-HaeIII digest in 10 µL). The increase in sample loading did not significantly affect the separation performance.

EXAMPLE 3

Separation of DNA Fragments Using a Single Equilibria Bulk Process

The separation of dsDNA fragments from a pUC18-DNA HaeIII digest was performed using the same beads as used in EXAMPLES 1 and 2. Nine different vials each containing 0.035 g of beads and 10 µL of DNA digest (4.5 µg) were mixed with 100 µL of 0.1 M triethylammonium acetate (TEAA), each vial containing different amounts of ACN. The incubation time was 10 min at 23° C. The vials were centrifuged with a Brinkman model 3200 table-top centrifuge for 5 minutes. A 3 µL aliquot of the supernatant was removed by syringe for analysis. The analysis was done using HPLC with on-line UV detection at 260 nm. TABLE 1 shows the concentration of DNA, TEAA, ACN and the amount of resin in the different experiments.

TABLE I

| Exp. | Amount of resin (g) | Volume (µL) | % ACN | TEAA | DNA (µg/µL) |
|---|---|---|---|---|---|
| 1 | 0.035 | 110 | 7.88% | 0.1M | 0.0405 |
| 2 | 0.035 | 110 | 9.01% | 0.1M | 0.0405 |
| 3 | 0.035 | 110 | 10.14% | 0.1M | 0.0405 |
| 4 | 0.035 | 110 | 11.26% | 0.1M | 0.0405 |
| 5 | 0.035 | 110 | 12.39% | 0.1M | 0.0405 |
| 6 | 0.035 | 110 | 13.51% | 0.1M | 0.0405 |
| 7 | 0.035 | 110 | 14.64% | 0.1M | 0.0405 |
| 8 | 0.035 | 110 | 15.91% | 0.1M | 0.0405 |
| 9 | 0.035 | 110 | 17.05% | 0.1M | 0.0405 |

Figure 6:
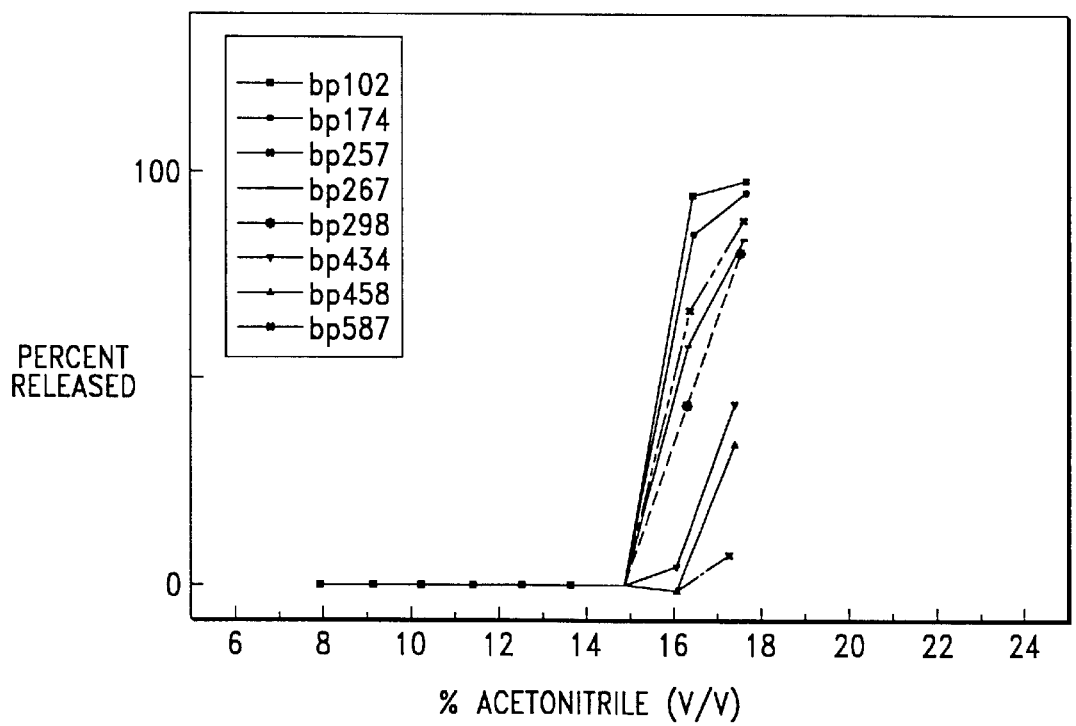
FIG. 6 shows the release of eight DNA fragments from polymer beads in single equilibria bulk separations (under conditions as described in TABLE 1) showing the dependence on the acetonitrile concentration.

Referring to FIG. 6, the experiments showed that the smaller fragments (80, 102, 174 bp) in this particular digest were released quantitatively from the resin surface by increasing the ACN concentration from 15 to 16% (in solution) and the larger fragments (257, 267, 298, 434, and 587 bp) by increasing the ACN concentration from 16 to 18.5%. Quantitative release for the 102 bp fragment was achieved by increasing the ACN concentration from 14.6% to 15.9%.

EXAMPLE 4

Separation of DNA Fragments Using Discs

FIG. 5 shows the separation of dsDNA fragments from a pUC18-DNA HaeIII digest performed using 8 micron C-18 nonporous poly(styrene-divinylbenzene) polymer beads in two discs placed in series. The discs are available commercially under the trademark Guard Disc™ (Transgenomic, Inc., San Jose, Calif.) which contain beads enmeshed in a web of TEFLON™ fibril matrix at a weight ratio of 9:1 beads to fibril matrix.

The DNA separation was run under the following conditions: Guard Disc™ 0.7×4.6 mm i.d.; stripping solvent 0.1 M TEAA, pH 7.2; gradient: 35–55% acetonitrile (ACN) in 3 min, 55–65% ACN in 7 min, 65% ACN for 2.5 min; 100% ACN for 1.5 min, back to 35% ACN in 2 min. The flow rate was 0.75 mL/min, detection UV at 260 nm, column temp. 51° C., p=50 psi. The sample was 3 μL (=0.12 μg pUC18 DNA-HaeIII digest).

EXAMPLE 5

Separation of PCR Reaction Products Using Discs

The reaction products of a PCR preparation are separated under the conditions as described in EXAMPLE 4. Primer dimers elute in about 2–3 minutes and are well resolved from a 405 base pair PCR product which elutes in about 4–5 minutes.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

What is claimed is:

1. A batch process for obtaining single-stranded polynucleotide fragments having a selected size from a mixture of polynucleotide fragments, wherein the lengths of said fragments in said mixture are up to 600 bases, said process comprising:
   a) applying a solution of said mixture of polynucleotide fragments and a counterion agent to a binding medium having a hydrophobic surface;
   b) contacting the binding medium with a first stripping solvent and counterion agent, the first stripping solvent having a concentration of organic component sufficient to release from the binding medium all polynucleotide fragments having a size smaller than the selected size, and removing the first stripping solvent from the binding medium; and
   c) contacting the binding medium with a second stripping solvent having a concentration of organic component sufficient to release from the binding medium the polynucleotide fragments having the selected size, and removing the second stripping solvent from the binding medium.

2. The process of claim 1 wherein the binding medium is rinsed with fresh first stripping solvent following step b) to remove residual fragments having a size smaller than the selected size therefrom.

3. The process of claim 1 wherein said separation is by MIPC.

4. The process of claim 1 wherein said polynucleotides comprise single-stranded DNA.

5. The process of claim 1 wherein said polynucleotides comprise RNA.

6. The process of claim 2 wherein said polynucleotides comprise single-stranded DNA.

7. The process of claim 2 wherein said polynucleotides comprise RNA.

8. The process of claim 3 wherein said polynucleotides comprise single-stranded DNA.

9. The process of claim 3 wherein said polynucleotides comprise RNA.

10. The process of claim 1 wherein said process is carried out at a temperature in the range of 20° C. to 90° C.

11. The process of claim 1 wherein said process is carried out at a temperature in the range of 50° C. to 75° C.

* * * * *